United States Patent
Lee et al.

(10) Patent No.: US 8,470,442 B2
(45) Date of Patent: Jun. 25, 2013

(54) METAL NANOPARTICLES FUNCTIONALIZED WITH RATIONALLY DESIGNED COATINGS AND USES THEREOF

(75) Inventors: Thomas Randall Lee, Houston, TX (US); Hye Hun Park, Palo Alto, CA (US); Nam Hoon Kim, Goleta, CA (US)

(73) Assignee: University of Houston System, Houston, TX (US)

( * ) Notice: Subject to any disclaimer, the term of this patent is extended or adjusted under 35 U.S.C. 154(b) by 416 days.

(21) Appl. No.: 12/798,454

(22) Filed: Apr. 5, 2010

(65) Prior Publication Data
US 2010/0255311 A1     Oct. 7, 2010

Related U.S. Application Data

(60) Provisional application No. 61/211,865, filed on Apr. 3, 2009.

(51) Int. Cl.
*B32B 5/16*    (2006.01)
*B05D 7/00*    (2006.01)

(52) U.S. Cl.
USPC ........... 428/403; 427/215; 427/216; 427/200; 428/407

(58) Field of Classification Search
USPC ................. 428/403–407; 427/215, 216, 220
See application file for complete search history.

(56) References Cited

U.S. PATENT DOCUMENTS

| | | | |
|---|---|---|---|
| 6,743,639 B1 * | 6/2004 | Tondra et al. | 436/518 |
| 7,456,213 B2 * | 11/2008 | Heller | 514/452 |
| 2003/0207296 A1 * | 11/2003 | Park et al. | 435/6 |
| 2005/0074551 A1 * | 4/2005 | Huang et al. | 427/212 |
| 2007/0224241 A1 * | 9/2007 | Stayton et al. | 424/423 |
| 2008/0045401 A1 * | 2/2008 | Zhou et al. | 502/60 |
| 2008/0220531 A1 | 9/2008 | Stayton et al. | 436/73 |

OTHER PUBLICATIONS

Rogers et al, Selective, controllable, and reversible aggregation of polystyrene latex microspheres via DNA hydridization, Apr. 7, 2005.*
Thermo Scientific Brochure, Carboxy-PEG-Thiol Compounds, crica 2006.*
Hye Hun Park, Design, synthesis, and characterization of organic shell/metal core hybrid composites, ProQuest Dissertations and Theses, 2009.*

* cited by examiner

*Primary Examiner* — Hoa (Holly) Le
(74) *Attorney, Agent, or Firm* — Benjamin Aaron Adler

(57) ABSTRACT

The present invention provides a composition and method for functionalizing nanoparticles that enables them to undergo reversible aggregation/deaggregation. The aggregation properties of this new system are reversible and readily monitored by optical absorbance measurements with the possibility of electrical and/or magnetic monitoring as well. The outer portion of the coating material is functionalized with polyethylene glycol (PEG) entities that facilitate biocompatibility and stability both in solution and in the solid state. Also provided are nanoparticles functionalized with rationally designed free radical initiators to effect tailored polymer growth from the surface. These systems may be used for a broad variety of applications, including biosensing with real-time feedback.

28 Claims, 8 Drawing Sheets

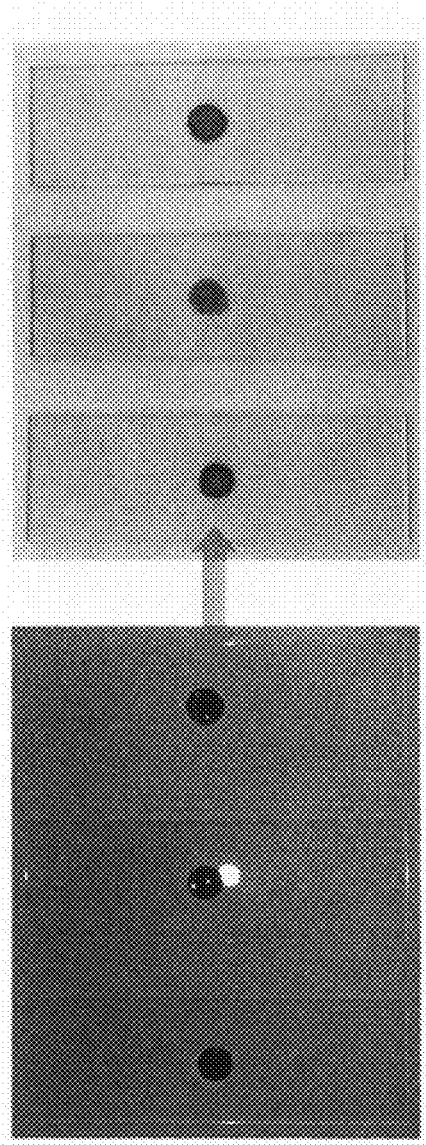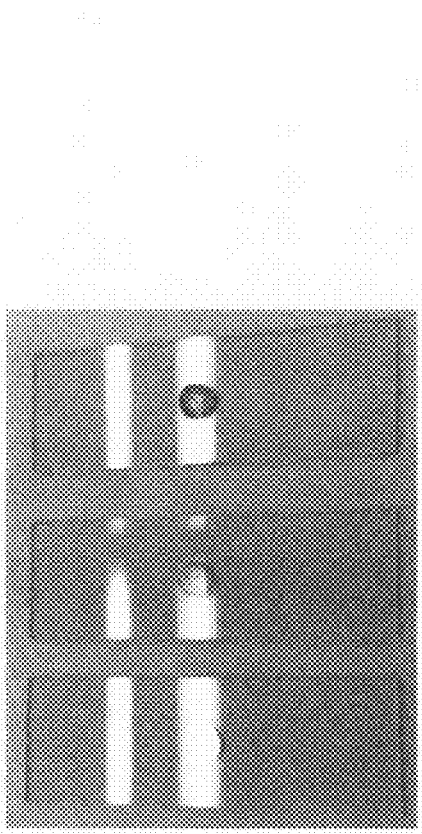
Fig. 6A
Fig. 6B
Fig. 6C

METAL NANOPARTICLES FUNCTIONALIZED WITH RATIONALLY DESIGNED COATINGS AND USES THEREOF

CROSS-REFERENCE TO RELATED APPLICATION

This non-provisional application claims the benefit under 35 U.S.C. §119(e) of provisional U.S. Ser. No. 61/211,865, filed Apr. 3, 2009, now abandoned, the entirety of which is hereby incorporated by reference.

BACKGROUND OF THE INVENTION

1. Field of the Invention

The present invention relates generally to the fields of surface chemistry and self-assembly materials. More particularly, the present invention relates to the design and synthesis of a stable and reversible system containing metal, alloy, or core/shell nanoparticles coated with a material that prevents irreversible aggregation of the nanoparticles and offers the possibility of radical initiation to effect tailored polymer growth from the surface.

2. Description of the Related Art

Metal and alloy nanoparticles, especially those comprised of noble metals in discrete form or in shell/core architectures, have been the focus of recent interest with regard to their potential applications in areas such as electronics, optics, biotechnology, and chemical catalysis. This heightened interest is mainly due to the size-dependent and shape-dependent optical and electrical properties and the amenability for the modification of the particle surface by taking advantage of strong ligand-metal interactions. The chemisorption of small molecules on the surface of metal nanoparticles (MNPs) frequently causes irreversible aggregation of the nanoparticles, and the resultant aggregates show distinct electronic, optical and biological properties from the individual metal nanoparticles. The change in these properties due to irreversible aggregation can be a major drawback for further practical applications owing to the unpredictable character of the resulting aggregates; however, controllable aggregation can be utilized in various technical applications, such as the assembly of nanoparticles, nanodevices, and colloidal sensors.

Metal nanoparticles with a radius much smaller than the incident wavelength of the light strongly absorb at certain wavelengths due to the resonance excitation of the surface plasmons, and these absorption bands are influenced by particle aggregation. When the metal nanoparticles aggregate, the distance between the particles becomes smaller, and the surface plasmon bands shift to longer wavelengths than those of the individual particles. The red shift of the metal nanoparticles can often be followed with the naked eye; for example, in the case of gold nanoparticles (AuNPs), the solution changes from pink-red to purple-blue. These color changes induced by the shorter interparticle distances provide a simple but effective method as a practical colorimetric tool for detecting specific reactions between anchored molecules on the gold nanoparticles and receptor molecules in the solution. Using these properties, it has been shown that gold nanoparticles modified with oligonucleotides aggregate through the hybridization of complementary oligonucleotide strands, providing a practical tool for the detection of targeted DNA sequences. Others have demonstrated the analytical capabilities of protein A-coated gold nanoparticles to determine the level of anti-protein A in serum samples. More recently, it has been shown that functionalizing gold nanoparticles with 2,2'-bipyridine and further complexing these nanoparticles with lanthanide metal ions such as europium and terbium could activate them as sensors for biologically important cations. Along with these specific examples, various approaches have been reported that demonstrate AuNP aggregates via hydrogen bonding, metal-ligand interactions, and ion paring.

The controlled reversible aggregation/deaggregation of metal nanoparticles is an important feature, especially where repeated use and in situ feedback are desired. Nevertheless, reversibility is difficult to realize as the aggregated metal nanoparticles tend to collapse and fuse irreversibly into larger particles. In most cases, the linkages between the aggregated metal nanoparticles cannot be separated to yield the initial constituent particles. To address this problem at least in part, external stimuli have been used to affect the aggregation/deaggregation of metal nanoparticles peripherally. These approaches can be broadly classified into three categories: temperature changes, pH changes, and molecular recognition.

Despite the significant amount of work on reversible processes that has been performed, more general and nonspecific routes are required to overcome the restrictions associated with the specific chemical routes for the development of aggregation-based sensors and the controlled assembly of metal nanoparticles for optoelectronics applications.

Thus, there is a recognized need in the art to design and synthesize metal nanoparticles functionalized with rationally designed coatings that enable their reversible aggregation/deaggregation. More specifically, the prior art is deficient in utilizing surface chemistry and coatings to affect reversible aggregation/deaggregation of metal nanoparticles. The present invention fulfills this long-standing need and desire in the art.

SUMMARY OF THE INVENTION

The present invention is directed to a composition that undergoes reversible aggregation/deaggregation. The composition is a nanoparticle functionalized with a sterically hindered coating material.

The present invention is also directed to a method of forming reversibly aggregating/deaggregating nanoparticles. The method comprises the step of functionalizing the nanoparticles with a sterically hindered coating material.

The present invention is also directed to a coating material used to enable the reversible aggregation/deaggregation of nanoparticles. The coating material comprises a headgroup used to anchor the coating molecules on the surface of the nanoparticle, a bio-inert functional group used to stabilize the nanoparticle by steric hindrance, and a variable length body of the coating material that connects the headgroup to the functional group.

BRIEF DESCRIPTIONS OF THE DRAWINGS

FIGS. 5A-5D show photographs of the HSPEG750-functionalized AuNPs with 20, 40, and 90 nm diameters from left to right: (FIG. 5A) in aqueous solution, (FIG. 5B) in solvent-free form, (FIG. 5C) SEM images of the citrate reduced 40 nm AuNPs, and (FIG. 5D) the HSPEG750-functionalized 40 nm AuNPs in solvent-free form.

FIGS. 6A-6C show photographs of the HSPEG750-functionalized AuNPs with 20, 40 and 90 nm diameters from left to right: (FIG. 6A) in aqueous solution, (FIG. 6B) in solvent-free form, (FIG. 6C) in solvent-free form with light.

Figure 7A:
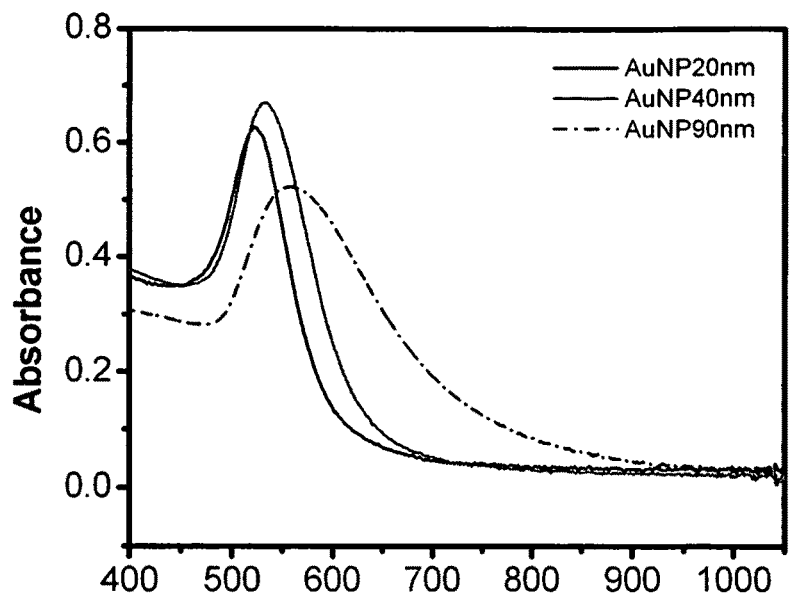
Figure 7B:
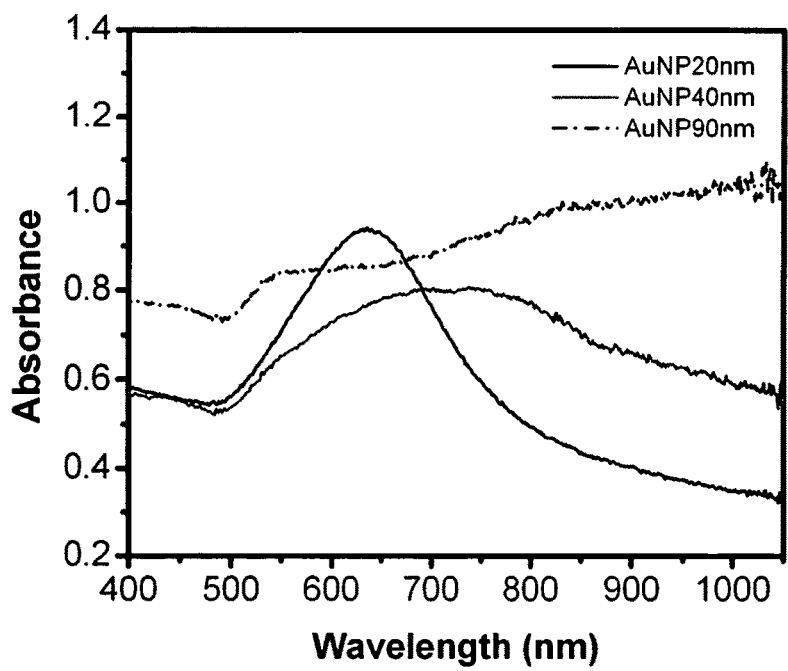

FIGS. 7A-7B show UV absorbance of the initiator-functionalized AuNPs (FIG. 7A) in aqueous solution and (FIG. 7B) in solvent-free form.

Figure 8A:
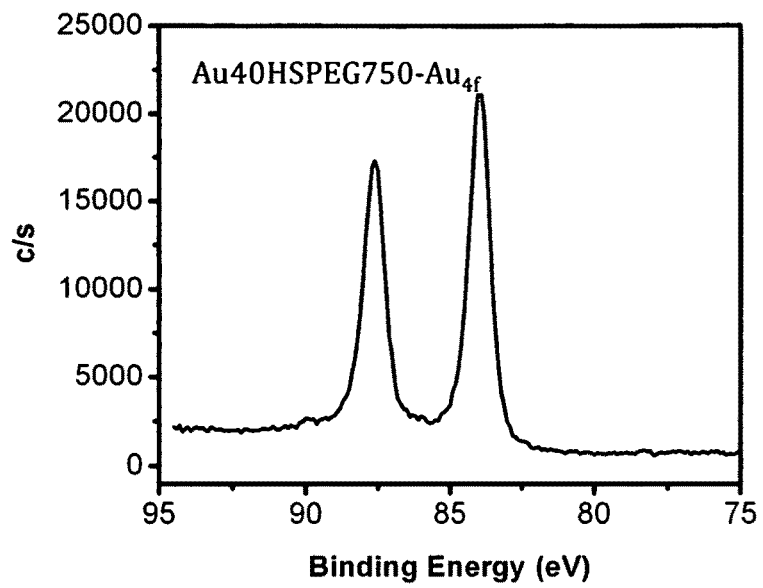
Figure 8B:
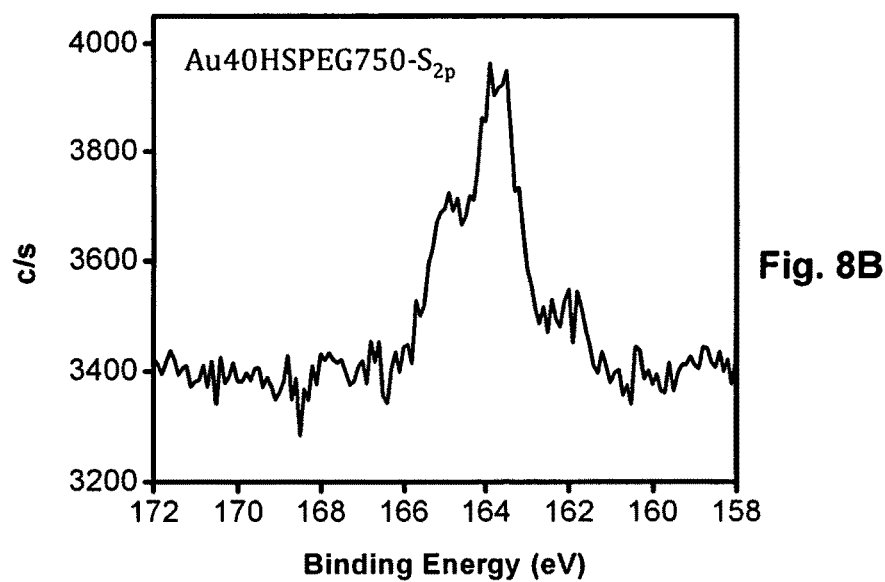

FIGS. 8A-8B show XPS spectra of the $Au_{4f}$ and $S_{2p}$ regions of the HSPEG750-functionalized 40 nm AuNPs.

DETAILED DESCRIPTION OF THE INVENTION

The use of the word "a" or "an" when used in conjunction with the term "comprising" in the claims and/or the specification may mean "one," but it is also consistent with the meaning of "one or more," "at least one," and "one or more than one." Some embodiments of the invention may consist of or consist essentially of one or more elements, method steps, and/or methods of the invention. It is contemplated that any method or composition described herein can be implemented with respect to any other method or composition described herein.

The use of the term "or" in the claims is used to mean "and/or" unless explicitly indicated to refer to alternatives only or the alternatives are mutually exclusive, although the disclosure supports a definition that refers to only alternatives and "and/or."

As used herein, the term "bio-inert" refers to the property of certain materials that do not initiate a tangible response or interact when introduced to biological tissue or system.

As used herein, the term "coating" refers to a covering that is applied to the surface of the nanoparticles.

As used herein, the terms "functional group" and "headgroup" are interchangeable and refer to a particular chemical moiety.

As used herein, the term "sterically hindered" refers to the spatial and size properties of certain chemical moieties that may restrict chemical reactivity and/or torsional bond angles.

In one embodiment of the present invention, there is provided a nanoparticle functionalized with a sterically hindered coating material that undergoes reversible aggregation/deaggregation. The nanoparticle may be a metal cluster, alloy cluster, metal oxide, quantum dot, nanorod, nanocage, nanodonut, or nanoshell. The nanoparticle may have a radius of about 1 nm to about 2000 nm. In the preferred embodiments, the nanoparticle may have a radius of about 10 nm to about 200 nm. The nanoparticle may be magnetic. The nanoparticle may be made from gold, silver, copper, platinum, iridium, osmium, palladium, rhodium, ruthenium, iron, cobalt, manganese, silica or an alloy or oxide thereof.

In a related embodiment, the coating is anchored to the surface of the nanoparticle by a headgroup. The coating material may comprise a headgroup used to anchor coating molecules on the surface of a nanoparticle, a bio-inert functional group used to stabilize the nanoparticle by steric hindrance, and a variable length body of the coating material that connects the headgroup to a terminal functional group or recognition moiety. The headgroup may be a thiol, disulfide, or related ligand. Representative functional groups include but are not limited to hydroxyl, methyl, ether, amine, and carboxylic acid. Representative bodies include but are not limited to oligoethylene glycol (OEG), polyethylene glycol (PEG), fluorocarbon, and hydrocarbon. The body may contain a radical initiator. The body may have a chain length between 3 and 10,000. In the preferred embodiment, a polyethylene glycol body has a chain length of about 350, 750, or 2000.

In yet another related embodiment, the coating is further modified with a recognition moiety on the surface of the nanoparticle. The recognition moiety may be a carbohydrate, peptide, antibody, enzyme, lectin, receptor, RNA, DNA, LNA, PNA, or molded plastic imprint.

In another embodiment of the present invention, there is provided a method of forming a reversible aggregating/deaggregating nanoparticle, comprising the step of functionalizing the nanoparticle with a sterically hindered coating material. The nanoparticle may be a metal cluster, alloy cluster, quantum dot, nanorod, nanocage, nanodonut or nanoshell. The nanoparticle may have a radius of about 1 nm to about 2000 nm. In the preferred embodiment, the nanoparticle may have a radius of about 10 nm to about 200 nm.

In a related embodiment, the coating comprises a headgroup used to anchor the coating molecules on the surface of a nanoparticle, a bio-inert functional group used to stabilize the nanoparticle by steric hindrance, and a variable length body of the coating material that connects the headgroup to a terminal functional group or recognition moiety. The headgroup may be a thiol, disulfide, or related ligand. Representative functional groups include but are not limited to hydroxyl, methyl, ether, amine, and carboxylic acid. Representative bodies include but are not limited to OEG, PEG, fluorocarbon, and hydrocarbon. The body may contain a radical initiator. The body may have a chain length between 3 and 10,000. In the preferred embodiment, the chain length may be about 350, 750 or 2000.

In yet another embodiment, there is provided a coating material used to functionalize reversible aggregation/deaggregation of nanoparticles, comprising a headgroup used to anchor the coating molecules on the surface of the nanoparticle, a bio-inert functional group used to stabilize the nanoparticle by steric hindrance, and a variable length body of the coating material that connects the headgroup to a terminal functional group or recognition moiety. The headgroup may be a thiol, disulfide, or related ligand. Representative functional groups include but are not limited to hydroxyl, methyl, ether, amine and carboxylic acid. Representative bodies include but are not limited to OEG, PEG, fluorocarbon, and hydrocarbon. The body may contain a radical initiator. The body may have a chain length between 3 and 10,000. In the preferred embodiment, the chain length may be about 350, 750, or 2000.

One purpose of this invention to design and synthesize nanoparticles functionalized with rationally designed coatings that permit the reversible aggregation/deaggregation of the nanoparticles. More specifically, the present invention utilizes (1) a headgroup (e.g., thiol) at one end of a molecular chain to anchor the individual coating molecules on the surface of a metal nanoparticle and (2) a molecular chain (e.g., PEG) to stabilize the metal nanoparticles by steric hindrance. The reversible aggregation/deaggregation of the resulting conjugates is demonstrated herein using a broad range of AuNP sizes and PEG molecular weights. Further modification of the coating with recognition species such as carbohydrates, peptides, antibodies, enzymes, and DNA allows for additional applications as biosensors with greater flexibility in the selection of both the targeting and receptor molecules.

Another purpose of this invention is to design and synthesize metal nanoparticles with coatings that offer prolonged shelf life and the ability to grow selected polymers from the surface via radical polymerization. More specifically, one end of the coating molecule is functionalized with a headgroup for binding to the metal nanoparticle surface, the middle part contains a radical initiator moiety that can be used to effect polymerizations, and the other end is functionalized with PEG or a related body to lend bio-inertness and steric stabilization against irreversible nanoparticle aggregation.

The present method can be generally applied to other nanoparticle systems such as quantum dots, noble metals (in any shapes, including spherical metal nanoparticles, nanorods, nanocages, nanoshells, nanodonuts, etc.), alloys (in any shapes, including spherical metal nanoparticles, nanorods, nanocages, nanoshells, nanodonuts, etc.), magnetic nanoparticles of all shapes, sizes, and configurations, any types of particles that can interact strongly and associatively with the specified coating molecule, shell/core structured nanoparticles (including any metal shell/core, any alloy shell/core, any dielectric shell/core, any magnetic nanoparticle including those with shell/core geometries, and any combinations thereof); providing great flexibility in the selection of the nanoparticles to be encapsulated with various kinds of polymer layers. For example, the PEG chain length —$(CH_2CH_2O)_n$— can range anywhere between n=3 and n=10,000. The recognition moiety in the present invention is chosen depending on what type of assay is needed. For example, some of these assays rely on specific bioaffinity recognition reactions, where generally natural biological binding components are used to form the specific binding assay (with biological binding components such as carbohydrates, peptides, antibodies, natural hormone binding proteins, lectins, enzymes, receptors, DNA, RNA, LNA, or PNA) or artificially produced binding compounds like genetically or chemically engineered carbohydrates, peptides, antibodies, molded plastic imprint (molecular imprinting), and receptors. Other assays rely on activity or modulation of the activity of compounds present in the sample or added into the reaction (e.g., biologically active enzymes, chemical compounds with activity on biological molecules, enzyme substrates, enzyme activators, enzyme inhibitors, enzyme modulating compounds) and so on.

Overall, the present invention provides useful insight to the assembly of stable free radical initiator/metal nanoparticle conjugates capable of being encapsulated into polymer shells, leading to a variety of technical applications, including reversible aggregation/deaggregation.

The following examples are given for the purpose of illustrating various embodiments of the invention and are not meant to limit the present invention in any fashion.

EXAMPLE 1

Immobilization and Characterization of HSPEG on the Surface of AuNPs

This section describes the functionalization of nanoparticle surfaces with a series of (PEG)-modified free radical initiators, generated with various chain lengths of PEG moieties on one end of the initiator. The bulky PEG group stabilizes gold nanoparticles by providing steric hindrance against aggregation of the gold nanoparticles. Using analysis by UV-vis spectroscopy, the stability of the resulting initiator-functionalized gold nanoparticles in solution was explored as a function of gold nanoparticle size (20, 40, and 90 nm in diameter) as well as the PEG chain length (Mn 350, 750, and 2000). The chemisorption and the conformational order of the initiator on the surface of gold nanoparticles were further characterized by X-ray photoelectron spectroscopy (XPS) and Fourier transform infrared (FTIR) spectroscopy, respectively. This approach illustrates the first step toward developing stable, free radical initiator-functionalized gold nanoparticles for future polymerization reactions around the gold nanoparticles, a method that can be generally applied to a variety of nanoparticle systems, including gold shell/silica core and gold shell/magnetic core nanoparticles.

Materials

For the initiator synthesis, 4,4'-azobis(4-cyanovaleric acid) (Aldrich, 75+%), 1,6-hexanedithiol (Aldrich, 96.0%), poly (ethylene glycol) methyl ether (Aldrich, Mn 350, 750, and 2,000), N,N'-dicyclohexylcarbodiimide (DCC, Fluka, 99.0%) and 4-dimethylaminopyridine (DMAP, Acros, 99.0%) were used as received. Tetrahydrofuran (THF, Mallinckrodt Baker) was freshly distilled over calcium hydride and collected immediately prior to use. Absolute ethanol (EtOH) was purchased from McCormick Distilling Co. and used without any purification. Hexanes, ethyl acetate, chloroform ($CHCl_3$), dichloromethane ($CH_2Cl_2$), and methanol (MeOH) were purchased from Mallinckrodt Baker and used without further purification. In the preparation of gold nanoparticles, trisodium citrate (EM Sciences, 99.0%), and hydrogen tetrachloroaurate (Strem, 99.9%) were used without purification. All water used in the reactions was purified to a resistance of 10 MΩ (Milli-Q Reagent Water System, Millipore Corporation) and filtered through a 0.2 mm filter to remove any particulate matter.

Synthesis of (R)-4-cyano-4-((E)-((R)-2-cyano-5-(6-mercaptohexylthio)-5-oxopentan-2-yl)diazenyl)pentanoic acid (HS-NN-)

Figure 1:
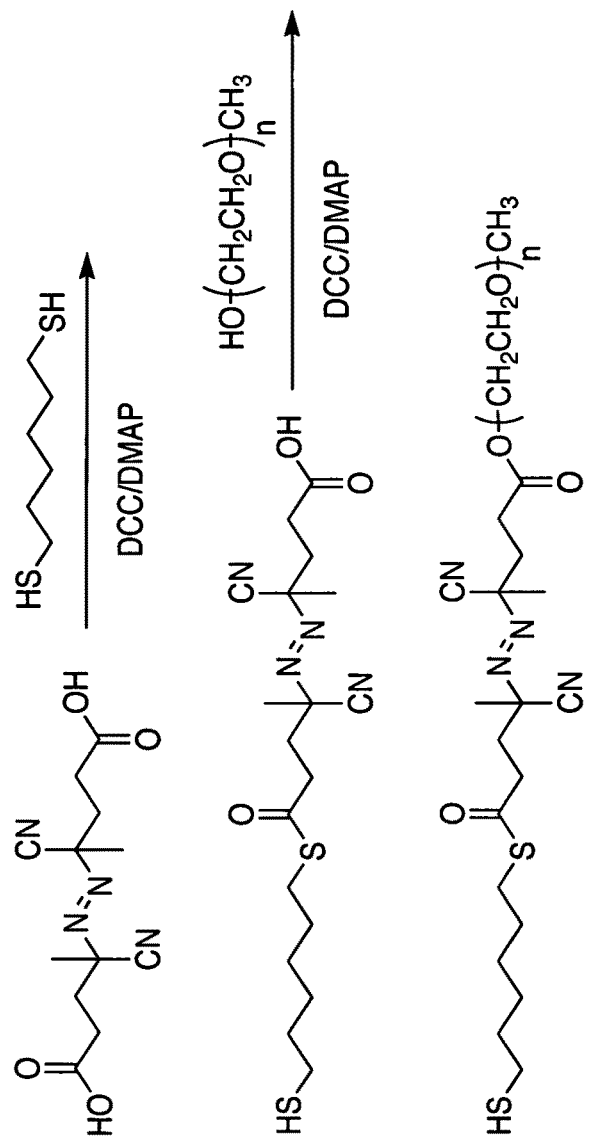
FIG. 1 shows a synthesis scheme for the Initiators (HSPEG350, HSPEG750, and HSPEG2000, where n=~7, 16, and 45, respectively).

FIG. 1 shows the synthesis of (R)-4-cyano-4-((E)-((R)-2-cyano-5-(6-mercaptohexylthio)-5-oxopentan-2-yl)diazenyl) pentanoic acid (HS-NN-). One end of 4,4'-azobis(4-cyanovaleric acid) was modified with 1,6-hexanedithiol using a DCC/DMAP reaction. Under an atmosphere of argon, 5 g of 4,4'-azobis(4-cyanovaleric acid) and 50 mg of DMAP were dissolved in 2.68 g of 1,6-hexanedithiol and 70 mL of anhydrous tetrahydrofuran (THF). The solution was cooled to 0° C. and 3.68 g of DCC in 50 mL THF was added dropwise to the mixture with stirring. The reaction mixture was allowed to react at 0° C. for 30 min, and then warmed to room temperature and stirred for 24 h under an atmosphere of argon. The urea precipitate was removed by filtration, and after the solvent was evaporated, the product was further purified by column chromatography 6/4 hexanes/ethyl acetate as eluent. The products were analyzed by $^1H$ NMR spectroscopy, and the results showed that the molecules were successfully synthesized. Yield: 60% $^1H$ NMR (in $CDCl_3$, δ in ppm): 2.89 (2H, t, 6.9 Hz), 2.49 (10H, m), 1.73 (3H, s), 1.68 (3H, s), 1.58 (4H, p, 7.2 Hz), 1.38 (4H, m).

Synthesis of (E)-PEG350-4-cyano-4-((E)-((R)-2-cyano-5-(6-mercaptohexylthio)-5-oxopentan-2-yl) diazenyl)pentanoic acid (HSPEG350)

The other end of the pure thiolated acid (HS-NN-) was further modified with a PEG350 group using a DCC/DMAP method. 1 g of the pure thiolated acid and 0.849 g of poly (ethylene glycol) methyl ether (Mn 350, PEG350) and 30 mg of DMAP were dissolved in 50 mL of anhydrous THF under an atmosphere of argon. The solution was cooled to 0° C., and 0.6 g of DCC in 30 mL THF was added dropwise to the mixture with stirring. The reaction mixture was allowed to react at 0° C. for 30 min, and then warmed to room temperature and stirred for 24 h under an atmosphere of argon. The urea precipitate was removed by filtration, and the filtrate was poured into saturated sodium bicarbonate, extracted with $CH_2Cl_2$, and dried over magnesium sulfate. After the solvent was evaporated, the product was further purified by column chromatography using 95/5 $CH_2Cl_2$/MeOH as eluent. The products were analyzed by $^1H$ NMR spectroscopy, and the results showed that the molecules were successfully synthesized. Yield: 30% $^1H$ NMR (in $CDCl_3$, δ in ppm): 4.26 (2H, t, 3.3 Hz), 3.73-3.53 (35H, m), 3.38 (3H, s), 2.89 (2H, t, 6.9 Hz), 2.49 (10H, m), 1.73 (3H, s), 1.68 (3H, s), 1.58 (4H, p, 7.2 Hz), 1.38 (4H, m).

Synthesis of (E)-PEG750-4-cyano-4-((E)-((R)-2-cyano-5-(6-mercaptohexylthio)-5-oxopentan-2-yl)diazenyl)pentanoic acid (HSPEG750)

To synthesize HSPEG750, the other end of the pure thiolated acid was further modified with a PEG750 group using a DCC/DMAP method in a similar manner to the synthesis of HSPEG350. After the reaction, the urea precipitate was removed by filtration, and the filtrate was poured into saturated sodium bicarbonate, extracted with $CH_2Cl_2$, and dried over magnesium sulfate. The solvent was evaporated, and the product was further purified by column chromatography using 95/5 $CH_2Cl_2$/MeOH as eluent. The products were analyzed by $^1H$ NMR spectroscopy, and the results showed that the molecules were successfully synthesized. Yield: 30% $^1H$ NMR (in $CDCl_3$, δ in ppm): 4.26 (2H, t, 3.3 Hz), 3.75-3.53 (70H, m), 3.38 (3H, s), 2.89 (2H, t, 6.9 Hz), 2.49 (10H, m), 1.73 (3H, s), 1.68 (3H, s), 1.58 (4H, p, 7.2 Hz), 1.38 (4H, m).

Synthesis of (E)-PEG2000-4-cyano-4-((E)-((R)-2-cyano-5-(6-mercaptohexylthio)-5-oxopentan-2-yl)diazenyl)pentanoic acid (HSPEG2000)

HSPEG2000 was synthesized in a manner analogous to that described above; the other end of the pure thiolated acid was modified with a PEG2000 group using DCC/DMAP method. After the reaction, the urea precipitate was removed by filtration, and the filtrate was poured into saturated sodium bicarbonate, extracted with $CH_2Cl_2$ and dried over magnesium sulfate. The solvent was evaporated and the product was further purified by column chromatography using 90/10 $CH_2Cl_2$/MeOH as eluent. The products were analyzed by $^1H$ NMR spectroscopy, and the results showed that the molecules were successfully synthesized. Yield: 20% $^1H$ NMR (in $CDCl_3$, δ in ppm): 4.26 (2H, t, 3.3 Hz), 3.79-3.49 (196H, m), 3.38 (3H, s), 2.89 (2H, t, 6.9 Hz), 2.49 (10H, m), 1.73 (3H, s), 1.68 (3H, s), 1.58 (4H, p, 7.2 Hz), 1.38 (4H, m).

Preparation of AuNPs

Three different sizes of gold nanoparticles (~20 nm, 40 nm, and 90 nm in diameter) were prepared by the conventional citric acid reduction of $HAuCl_4$ in water with trisodium citrate at near-boiling temperature. The size of gold nanoparticles was characterized by scanning electron microscopy (SEM) and dynamic light scattering (DLS). All glassware used in the preparation and storage of the gold nanoparticles was treated with aqua regia, rinsed with purified water, and cleaned with piranha solution (7:3 concentrated $H_2SO_4$/30 wt % $H_2O_2$).

Characterization of the Synthesized Initiators, AuNPs, and Initiator-Functionalized AuNPs Nuclear magnetic resonance (NMR) spectra were recorded on a General Electric QE-300 spectrometer operating at 300 MHz for $^1H$. The data were obtained in $CDCl_3$ and referenced to δ 7.26 for $^1H$ spectra of the synthesized initiators. To characterize the bare gold nanoparticles and initiator-functionalized gold nanoparticles, ultraviolet-visible (UV-vis) spectroscopy, X-ray photoelectron spectroscopy (XPS), scanning electron microscopy (SEM) and dynamic light scattering (DLS) were used.

The optical properties of the gold nanoparticles and the initiator-functionalized gold nanoparticles were monitored at room temperature using a Cary 50 Scan UV-vis optical spectrometer (Varian) with Cary Win UV software employed. For the UV-vis studies, 1 mL of each AuNP solution (24 nm; $\sim3\times10^{11}$ particles/mL, 40 nm; $\sim8\times10^{10}$ particles/mL, 90 nm; $\sim7\times10^9$ particles/mL) was diluted twice with distilled $H_2O$ in glass vials. Subsequently, 0.3 mL of the initiator solution (HS-NN-, 1 mM) in EtOH was added to the gold nanoparticle solutions (24, 40 and 90 nm in diameter), respectively, and the mixtures were immediately agitated before recording the optical spectra to ensure the homogeneity of the solution. This procedure was performed for each of the different length initiators (HSPEG350, HSPEG750, and HSPEG2000). UV-vis spectra of the prepared gold nanoparticles were collected by transferring them to a quartz cuvette having a 1 cm optical path length and scanning over a range of wavelengths (400-1000 nm). Spectroscopic data were collected as a function of time. Gold nanoparticles modified with HS-NN- aggregated immediately, which contrasts with the behavior of those modified with HSPEG350, HSPEG750, and HSPEG2000.

XPS spectra of the initiator-functionalized gold nanoparticles were collected using a PHI 5700 X-ray photoelectron spectrometer equipped with a monochromatic Al Kα X-ray source (hv=1486.7 eV) incident at 90° C. relative to the axis of a hemispherical energy analyzer. Three different sizes of the gold nanoparticles were modified with HSPEG750. 10 mL of the aqueous suspension of AuNPs (20, 40, and 90 nm in diameter) was mixed with a 1 mM solution of HSPEG750 in EtOH (3 mL) for 30 min, and this mixture was allowed to stand at room temperature for 24 h. To remove the unbound initiators, the final mixture was washed by centrifugation at 8,000, 6,000, and 3,000 rpm for 20, 40, and 90 nm gold nanoparticles, respectively, for 30 min, twice with water, and twice with ethanol before use. The initiator-functionalized gold nanoparticles were then deposited onto a silicon wafer, and the solvent was allowed to evaporate before analysis. The spectrometer was operated at high resolution with pass energy of 23.5 eV, a photoelectron takeoff angle of 45° from the surface, and an analyzer spot diameter of 2 nm. The base pressure in the chamber during the measurements was $3\times10^{-9}$ Torr, and the spectra were collected at room temperature. Two, eight, and forty scans were accumulated to obtain the $Au_{4f}$, $C_{1s}$ and $S_{2p}$ spectra, respectively. After collecting the data, the binding energies of the S and C peaks were referenced by setting the $Au_{4f7/2}$ binding energy to 83.8 eV.

Analysis by SEM was performed using a LEO Scanning Electron Microscope with 20 kV of the accelerating voltage during the measurements. Bare AuNPs and initiator-functionalized gold nanoparticles were deposited on silicon wafers and dried at room temperature to collect the images. SEM was used to examine the overall morphology of the gold nanoparticles and initiator-functionalized gold nanoparticles.

For the DLS measurements, an ALV-5000 Multiple Tau Digital Correlation instrument was used, operating at a light source wavelength of 514.4 nm and a fixed scattering angle of 90°. The diameter of the gold nanoparticles and the initiator-functionalized gold nanoparticles were measured at room temperature. The samples were analyzed at dilute concentrations, and all of the collected data showed good Gaussian distribution curves.

Stability Evolution of the Initiator-Functionalized AuNPs

The stability of the initiator-functionalized gold nanoparticles was thoroughly investigated using UV-vis spectroscopy. According to Mie theory, gold nanoparticles with a radius much smaller than the incident wavelength of the light will absorb at certain wavelengths due to the resonance excitation of the surface plasmons. These absorption bands are strongly influenced by the particle shape, size and the surrounding medium along with particle aggregation. In general, the surface plasmon resonance (SPR) band of Au spheres (about 10~50 nm in diameter) appears at around 530 nm, and an increase in diameter from 10 up to 100 nm shows a red-shift of up to ~40 nm in wavelength. The formation of a dielectric layer around the gold nanoparticles will result in a red shift of the SPR band, if the dielectric constant of the layer is larger than that of the medium. In addition, when the gold nanoparticles aggregate and the distance between aggregating particles becomes small compared to the particle radius, the SPR band will appear at longer wavelengths than those of the individual particles. This shift is mostly accompanied with broadening and a decrease in the intensity of the SPR bands. Therefore, the detailed features of SPR peaks provide clues regarding changes of surface state and aggregation for gold nanoparticles.

The formation and the stability of the AuNP-initiator conjugates were studied by monitoring the SPR band in the UV-vis spectra as a function of time (FIGS. 2A-2C, 3A-3C and 4A-4C). To investigate the effect of the length of the PEG groups, three series of experimental sets were studied. In the first set, the size of the gold nanoparticles was kept constant at ~20 nm, whereas the PEG chain length of the initiators were varied. Similarly, in the second and third set of the experiments, the sizes of the gold nanoparticles were kept constant at ~40 and 90 nm respectively, and the chain length of the initiators was varied.

Figure 2A:
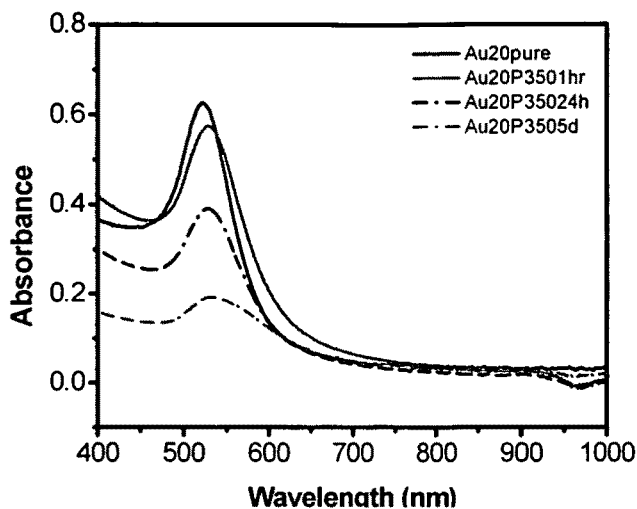
FIGS. 2A-2C shows UV absorbance of bare and initiator-functionalized 20 nm AuNPs as a function of increasing time in solution.
Figure 2B:
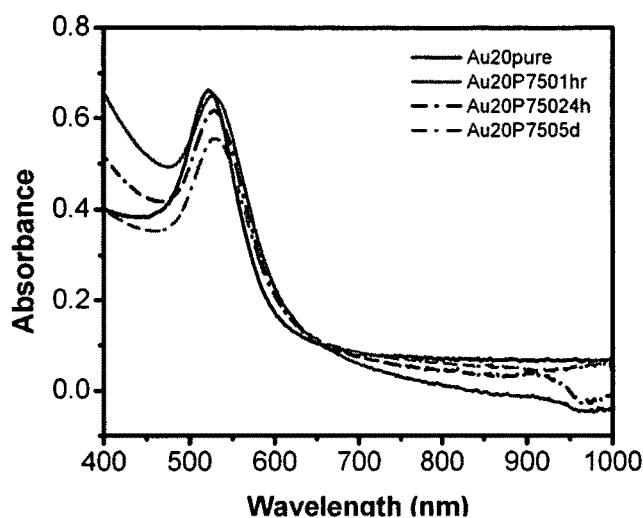
Figure 2C:
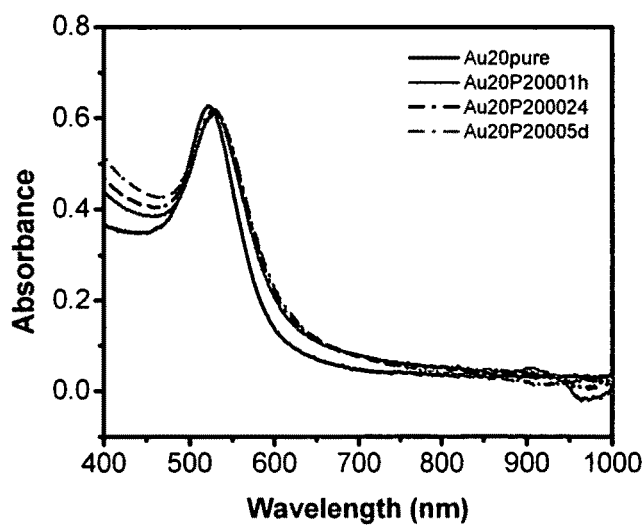

FIGS. 2A-2C show the optical spectra of the 20 nm gold nanoparticles modified with different length initiators. The spectrum for the as-prepared 20 nm gold sol is also shown for comparison. In each case, the SPR gradually red-shifted from 524 nm as the initiators were added to the gold nanoparticle solutions regardless of the chain lengths of the initiators, indicating the immobilization of the molecules on the surface of the gold nanoparticles. This observation is consistent with the formation of an adsorbed organic layer around the metal nanoparticles in solution. For the 20 nm gold nanoparticles modified with the shortest PEG chain, gold nanoparticles-HSPEG350 conjugates, the gold nanoparticles started aggregating in 24 h and all of the conjugate precipitated within 5 days. This aggregation gives rise to the dramatic decrease in the extinction maximum in the SPR band as shown in FIG. 2A. Importantly, however, the rate of the aggregation was much slower for the 20 nm gold nanoparticles functionalized with longer PEG chain initiators when compared to the gold nanoparticles-HSPEG350. Interestingly, the 20 nm gold nanoparticles-HSPEG2000 conjugates with the longest PEG chains showed almost no noticeable broadening or decrease in the intensity of the SPR peak, implying that the gold nanoparticles undergo little or no aggregation upon adsorption of the HSPEG2000 in solution for up to 5 days.

Figure 3A:
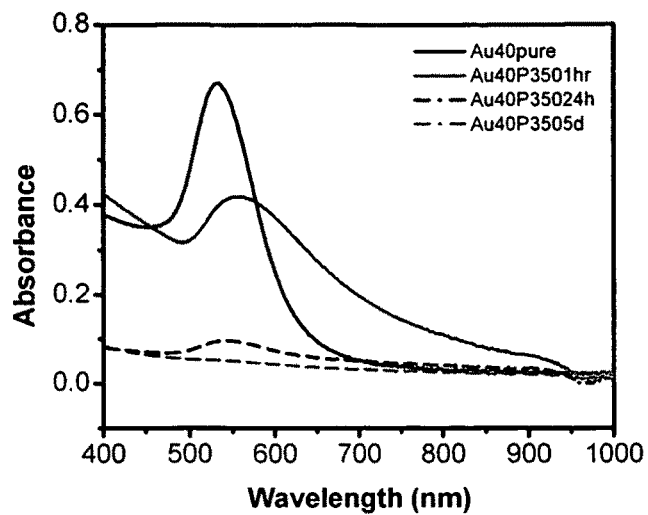
FIGS. 3A-3C shows UV absorbance of bare and initiator-functionalized 40 nm AuNPs as a function of increasing time in solution.
Figure 3B:
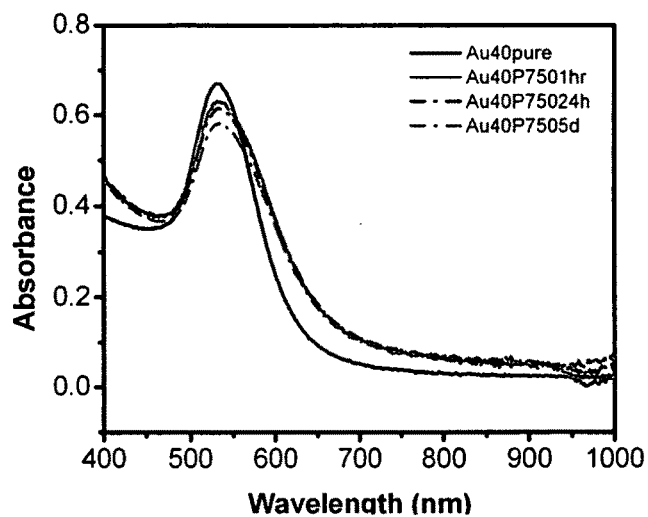
Figure 3C:
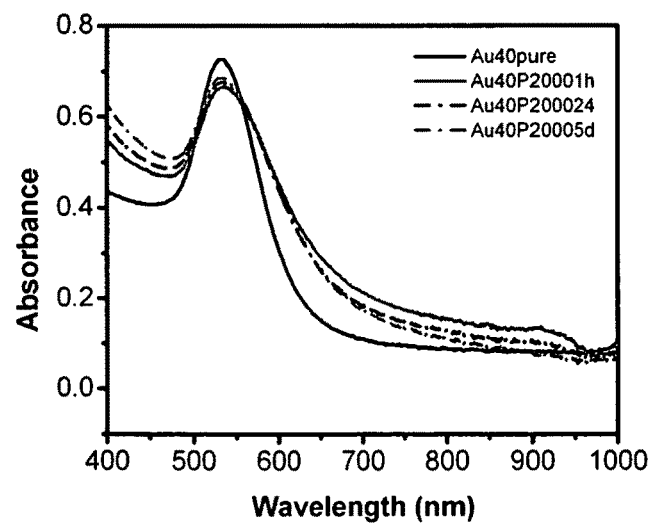

Chain length effects of the PEG groups were more clearly observed with the larger sizes of the gold nanoparticles as shown in FIGS. 3A-3C and 4A-4C. FIGS. 3A-3C show the optical spectra of the 40 nm gold nanoparticles modified with different length initiators. The spectrum for the as-prepared gold sol is shown for comparison as well. Initially, the SPR bands of the gold nanoparticles red-shifted from 524 nm as the initiators were added to the 40 nm gold nanoparticle solutions regardless of the chain lengths of the initiators, as discussed previously. The rate of change of the SPR band was inversely dependent on the PEG chain length, similar to the 24 nm conjugate system, exhibiting the largest change with the shortest PEG chain.

Figure 4A:
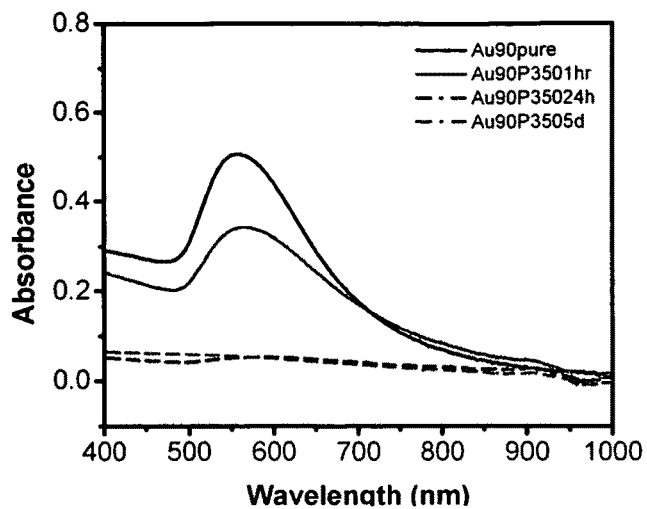
FIGS. 4A-4C shows UV absorbance of bare and initiator-functionalized 90 nm AuNPs as a function of increasing time in solution.
Figure 4B:
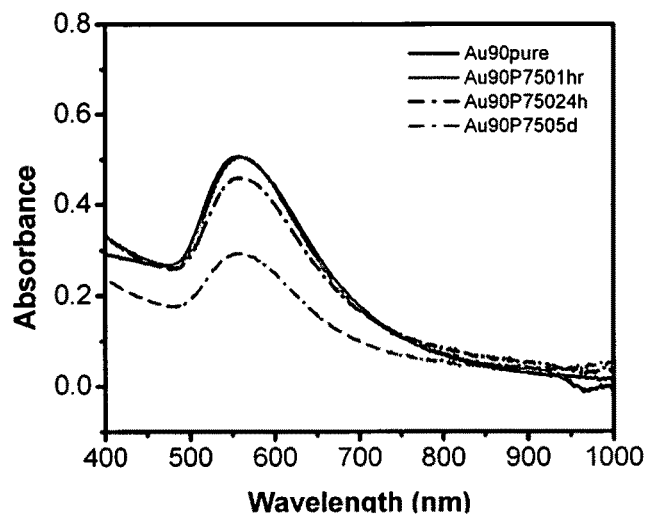
Figure 4C:
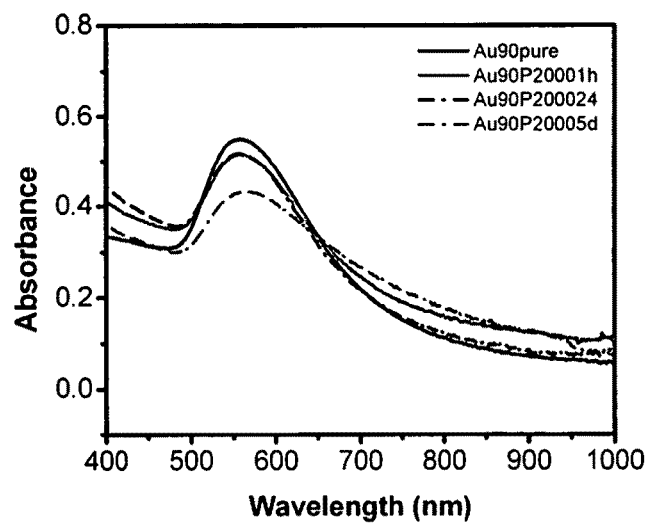

As shown in FIG. 3A, a dramatic red shifting and broadening of the SPR band to 585 nm was observed for the 40 nm gold nanoparticles modified with the shortest PEG chain initiators. It took only one hour for the SPR band to shift to 585 nm after adding the initiators, and substantial aggregation occurred as characterized by the broadening and the decreased intensity of the SPR band in 24 h. In contrast, the SPR bands of the 40 nm gold nanoparticles-HSPEG750 and 40 nm AuNPsPEG2000 conjugates show little or no broadening or decrease in the intensity of the SPR band, suggesting that the gold nanoparticles modified with the longer PEG chain initiators undergo almost no aggregation upon adsorption of the initiators. The 90 nm gold nanoparticles conjugates showed a similar trend as shown in FIGS. 4A-4C. The gold nanoparticles modified with the short initiators aggregated and precipitated in the solution, but the gold nanoparticles modified with the longer initiators were stable for at least 5 days.

In the UV-vis study, there were significantly different SPR bands in the spectral regions (400~1000 nm) for the gold nanoparticles-initiator conjugates containing PEG chains of different lengths. Generally, the SPR bands in the UV spectra of the gold nanoparticles-HSPEG350 conjugates were significantly broadened, red-shifted, and exhibited diminished intensity. The gold nanoparticles-HSPEG750 and gold nanoparticles-HSPEG2000 showed almost no changes in the UV spectra as a function of time. This observation also supports the notion of steric stabilization by the PEG groups for gold nanoparticles, which plays a role in their resistance to aggregation. These gold nanoparticles were synthesized with the reduction of auric acids in water using citrate molecules. During the process of immobilization of the initiators, citrate ions are displaced from the surface of the gold nanoparticles, thereby reducing the surface charge. Without the strong charge-charge repulsion, van der Waals-driven aggregation of the nanoparticles is the natural tendency of these systems seeking to minimize surface area. Such aggregation was effectively prevented by the steric hindrance provided with the bulky PEG groups covering the gold nanoparticle surface, in a similar way to synthetic polymers and biopolymers (e.g., proteins, gelatin). The initiator modified with PEG750 effectively stabilized various sizes of the gold nanoparticles (up to 90 nm in diameter) in water for several days. Indeed, the radius of the gold nanoparticles-HSPEG750 conjugates increased by 5 nm as the measured hydrodynamic radius of the particles in solution using the DLS, and the value is consistent with results reported previously. The overall results regarding the stability evolution of the initiator-functionalized gold nanoparticles are summarized in Table 1. The AuNPs-HSPEG750 conjugates were more thoroughly investigated as outlined below.

TABLE 1

|  | HSN = N | HSPEG350 | HSPEG750 | HSPEG2000 |
|---|---|---|---|---|
| AuNP 20 nm | unstable | stable | stable | stable |
| AuNP 40 nm | unstable | unstable | stable | stable |
| AuNP 90 nm | unstable | unstable | stable | stable |

EXAMPLE 2

Reversible Aggregation/Deaggregation of the Initiator-Functionalized AuNPs

As described in the preceding section, the initiator modified with PEG750 was able to stabilize the various sizes of the gold nanoparticles in water. More interestingly, it was possible to isolate the AuNPs-HSPEG750 conjugates in solvent-free form and re-dissolved them in aqueous solutions (pH 4, 7, and 10) or non-aqueous polar solvents such as EtOH, MeOH, THF, or $CH_2Cl_2$, without any change. However, the reversible aggregation/deaggregation behavior was not observed with the nonpolar solvent hexane, in the only example investigated.

FIGS. 5A-5D provide evidence of this phenomenon, showing (FIG. 5A) 20, 40, and 90 nm AuNPs-HSPEG750 conjugates dispersed in aqueous solution and (FIG. 5B) 20, 40, and 90 nm gold nanoparticles conjugates isolated in solvent-free form. Once the solvents were evaporated, the particles begin to aggregate, revealing the bulk metal color of gold, FIG. 5B. Moreover the isolating-re-dissolving process with the conjugates revealed that the aggregation/deaggregation was completely reversible; the gold nanoparticles-HSPEG750 conjugates did not undergo fusion of the metallic cores even in the solvent-free form, which is routinely observed for large AuNPs (>10 nm) and leads to irreversible aggregation. Instead, the dried conjugates were re-dissolved in the various solvents without any noticeable sign of particle degradation or formation of irreversible aggregates under these conditions.

FIG. 6A-6C provides additional information for these phenomena, where 20, 40, and 90 nm AuNPs-HSPEG750 conjugates were deposited and dried on flat glass plates. The bulk metal color of gold was more clearly seen in this experiment to support our previous observations. This reversible process provides strong evidence to conclude that HSPEG750 is successfully able to stabilize gold nanoparticles against irreversible aggregation, providing steric hindrance when it displaces citrate ions.

The optical properties of the reversibly aggregated/deaggregated HSPEG750-functionalized gold nanoparticles were thoroughly investigated using UV-vis spectroscopy. FIGS. 7A-7B show the optical spectra of the HSPEG750-functionalized gold nanoparticles in aqueous solution and in solvent-free form. The measurements for the solvent-free samples were performed on nanocomposite arrays formed on glass slides with unpolarized light at normal incidence. For three different sizes of the HSPEG750-functionalized gold nanoparticles, the SPR band dramatically red-shifted as the solvent evaporated, indicating smaller distances between the gold nanoparticles in the deposited array of the particles. Reversible aggregation/deaggregation of the nanoparticles was reflected in the reversible UV-vis spectra. This reversibility of the optical properties was repeated several times without any degradation of the absorbances.

Figure 5A:
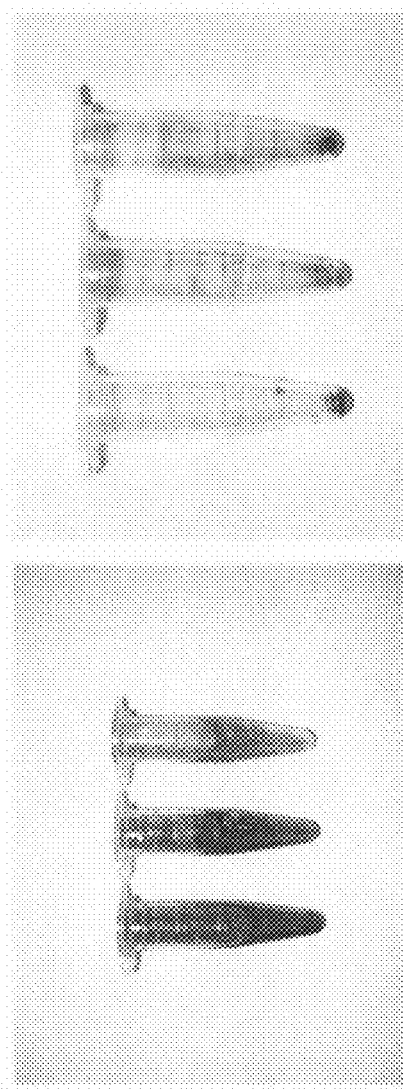
Figure 5B:
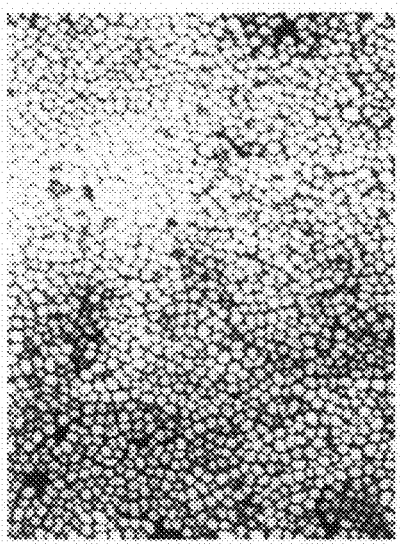
Figure 5C:
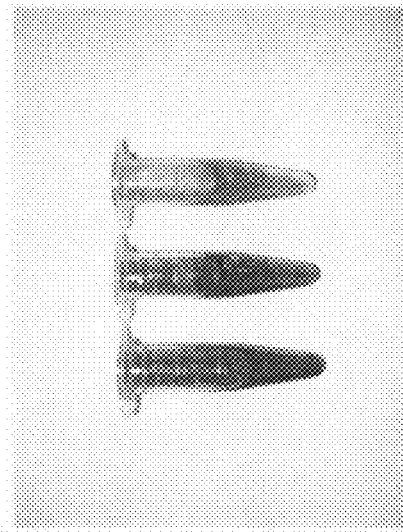
Figure 5D:
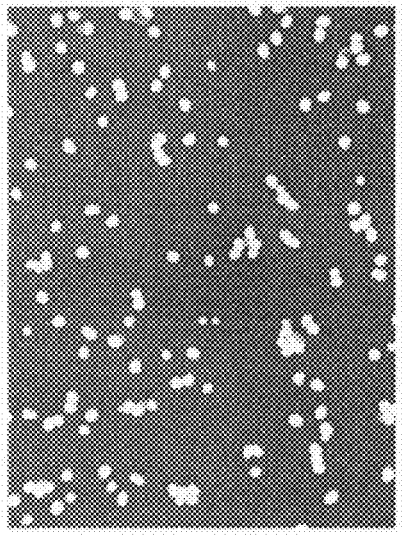

To assess the morphological changes caused by the immobilization of the HSPEG750, the 40 nm AuNPs-HSPEG750 composite samples were probed using SEM. FIGS. 5C-5D show SEM images corresponding to citrate-capped 40 nm gold nanoparticles and 40 nm AuNPs-HSPEG750 composites, respectively. Gold nanoparticles prepared by the citrate acid reduction method were nearly spherical in shape with a particle diameter of ~40 nm as expected. The HSPEG750-modified gold nanoparticles were also spherical in shape with the same particle size as the citrate-capped gold nanoparticles. In the case of the HSPEG750-modified gold nanoparticles, the nanoparticles were in extremely close proximity to each other, which is consistent with the observed color change from purple to gold (FIG. 5B) as the particles dry. The SEM images support the hypothesis that the HSPEG750 molecules provide steric hindrance, inhibiting the aggregation and fusion of the gold nanoparticles.

EXAMPLE 3

Immobilization of the HSPEG750 on the Surface of the AuNPs and Analysis by XPS

Citrate-capped gold nanoparticles as well as planar surfaces can be effectively grafted with a thiol end-capped monomer or polymer by simple contact of the gold surface with the solutions of the organic molecules because the covalent bond that forms between Au and S is stronger than the interaction between Au and citrate. The nature of the Au—S bonding in the composites can be evaluated by examining the binding energies of sulfur by X-ray photoelectron spectroscopy since the new bond (Au—S) influences the distribution of electrons in the atoms of interest. In particular, the $S_{2p}$ region of the XPS spectra can provide strong evidence for bond formation between the sulfur and the gold substrate, although spin-orbital coupling can inhibit an accurate analysis by producing a doublet with a split of 1.2 eV, either for bound or for free thiol sulfur; the binding energy of the $S_{2p3/2}$ peak for S bound to gold surfaces is known to be 162 eV, in contrast, the $S_{2p3/2}$ peak for unbound S appears at around 164 eV in the XPS spectra, which is also known as the characteristic energy of $S_{2p3/2}$ peak of thioester. Based on these precedents, XPS was used to confirm the immobilization of the HSPEG750 on the surface of the gold nanoparticles (20, 40, and 90 nm). XPS spectra for the 20, 40, and 90 nm gold nanoparticles-HSPEG750 composites were collected, and the binding energy (BE) scales for the organic layers on the gold nanoparticles were referenced by setting the $Au_{4f7/2}$ BE to 84 eV. For the purpose of illustration, the XPS spectra of the $Au_{4f}$ and $S_{2p3/2}$ region for the 40 nm gold nanoparticles-HSPEG750 are shown in FIG. 8A-8B. Covalent bonding between the HSPEG750 and the gold nanoparticles was verified by the observation of the $S_{2p3/2}$ peak at 162 eV for the 40 nm gold nanoparticles.

The strong $S_{2p3/2}$ signal at 164 eV can be rationalized either as an incomplete adsorbate binding of the HSPEG750 or the thioester sulfur found within the initiator chain. The latter is most likely to be responsible given the relative attenuation of photoelectrons and their different positions around the gold nanoparticles; bound-thiol sulfurs exists at the Au-HSPEG750 interface, and the thioester sulfurs are closer to the outer surface. In contrast to homogeneously distributed materials, attenuation in a layered structure tends to underestimate the elements buried deeper relative to those at the outer surface, leading to much smaller intensity for the buried atoms in the corresponding XPS spectra. The small intensity of the $S_{2p3/2}$ peak at 162 eV for the bound thiol sulfur in FIG. 7 can be understood in a similar way. Considering the presence of the $S_{2p3/2}$ peak at 164 eV, we cannot rule out the possibility of the presence of unbound HSPEG750 (unbound thiols); however, it is likely that the $S_{2p3/2}$ peak at 164 eV arises mainly from the thioester sulfur, and the HSPEG750s are largely if not completely adsorbed on the surface of the gold nanoparticles.

To rationalize this observation, HSPEG750s were also immobilized on a flat gold substrate, and the $S_{2p3/2}$ signal in XPS showed the same trend as the AuNPs-HSPEG750 system. These observations support the conclusion that the HSPEG750s are completely bound to the gold nanoparticles.

Any patents or publications mentioned in this specification are indicative of the levels of those skilled in the art to which the invention pertains. Further, these patents and publications are incorporated by reference herein to the same extent as if each individual publication was specifically and individually incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A composition that undergoes reversible aggregation/deaggregation, wherein said composition is a nanoparticle functionalized with a sterically hindered coating material, wherein said coating comprises:
   a headgroup used to anchor coating molecules on the surface of a nanoparticle; a bio-inert terminal functional group used to stabilize the nanoparticle by steric hindrance; and
   a variable length body of the coating material that connects the headgroup to a bio-inert terminal functional group and/or a recognition moiety, said moiety located near the terminal functional group, wherein the body contains a radical initiator.

2. The composition of claim 1, wherein said nanoparticle is a metal cluster, alloy cluster, metal oxide, quantum dot, nanorod, nanocage, nanodonut or nanoshell.

3. The composition of claim 1, wherein said nanoparticle has a radius of about of 1 nm to about 2000 nm.

4. The composition of claim 3, wherein said nanoparticle has a radius of about 10 nm to about 200 nm.

5. The composition of claim 1, wherein said nanoparticle is magnetic.

6. The composition of claim 1, wherein said nanoparticle is made from a metal of gold, silver, copper, platinum, iridium, osmium, palladium, rhodium, ruthenium, iron, cobalt, or manganese, said nanoparticle is made from silica, or said nanoparticle is made from an alloy or an oxide of said metal.

7. The composition of claim 1, wherein said headgroup is a thiol or a disulfide, or a chemically similar ligand.

8. The composition of claim 1, wherein said functional group is hydroxyl, methyl, ether, amine, and/or carboxylic acid.

9. The composition of claim 1, wherein said body is oligoethylene glycol (OEG), polyethylene glycol (PEG), fluorocarbon, and/or hydrocarbon.

10. The composition of claim 9, wherein said body has between 3 and 10,000 repeat units.

11. The composition of claim 1, wherein said coating material is (E)-PEG350-4-cyano-4-((E)-((R)-2-cyano-5-(6-mercaptohexylthio)-5-oxopenta-n-2-yl)diazenyl)pentanoic acid, (E)-PEG750-4-cyano-4-(E)-((R)-2-cyano-5-(6-mercaptohexylthio)-5-oxopenta-n-2-yl)diazenyl)pentanoic acid or (E)-PEG2000-4-cyano-4-((E)-((R)-2-cyano-5-(6-mercaptohexylthio)-5-oxopenta-n-2-yl)diazenyl)pentanoic acid or a chemically similar coating material.

12. The composition of claim 1, wherein the coating is further modified with a recognition moiety on the surface of the nanoparticle.

13. The composition of claim 12, wherein the recognition moiety is a carbohydrate, peptide, antibody, enzyme, lectin, receptor, RNA, DNA, LNA, PNA, or molded plastic imprint.

14. A method of forming a reversible aggregating/deaggregating nanoparticle, comprising the step of:
   functionalizing said nanoparticle with a sterically hindered coating material, wherein said coating comprises:
   a headgroup used to anchor coating molecules on the surface of a nanoparticle;
   a bio-inert terminal functional group used to stabilize the nanoparticle by steric hindrance: and
   a variable length body of the coating material that connects the headgroup to a bio-inert terminal functional group and/or a recognition moiety, said moiety located near the terminal functional group, wherein the body contains a radical initiator.

15. The method of claim 14, wherein said nanoparticle is a metal cluster, alloy cluster, metal oxide, quantum dot, nanorod, nanocage, nanodonut or nanoshell.

16. The method of claim 14, wherein said nanoparticle has a radius of about 1 nm to about 2000 nm.

17. The method of claim 16, wherein said nanoparticle has a radius of about 10 nm to about 200 nm.

18. The method of claim 14, wherein said headgroup is a thiol or a disulfide.

19. The method of claim 14, wherein said functional group is hydroxyl, methyl, ether, amine, and/or carboxylic acid.

20. The method of claim 14, wherein said body is oligoethylene glycol (OEG), polyethylene glycol (PEG), fluorocarbon, and/or hydrocarbon.

21. The method of claim 20, wherein said body has between 3 and 10,000 repeat units.

22. The method of claim 14, wherein said coating material is (E)-PEG350-4-cyano-4-((E)-((R)-2-cyano-5-(6-mercaptohexylthio)-5-oxopenta-n-2-yl)diazenyl)pentanoic acid, (E)-PEG750-4-cyano-4-((E)-((R)-2-cyano-5-(6-mercaptohexylthio)-5-oxopenta-n-2-yl)diazenyl)pentanoic acid or (E)-PEG2000-4-cyano-4-((E)-((R)-2-cyano-5-(6-mercaptohexylthio)-5-oxopenta-n-2-yl)diazenyl)pentanoic acid, or a chemically similar coating material.

23. A coating material used to enable the reversible aggregation/deaggregation of nanoparticles, comprising:
   a headgroup used to anchor the coating molecules on the surface of the nanoparticle;
   a bio-inert terminal functional group used to stabilize the nanoparticle by steric hindrance; and
   a variable length body of the coating material the connects the headgroup to a bio-inert terminal functional group and/or a recognition moiety, said moiety located near the terminal functional group, wherein the body contains a radical initiator.

24. The coating material of claim 23, wherein said headgroup is a thiol or a disulfide, or chemically similar ligand.

25. The coating material of claim 23, wherein said functional group hydroxyl, methyl, ether, amine, and/or carboxylic acid.

26. The coating material of claim 23, wherein said body is oligoethylene glycol (OEG), polyethylene glycol (PEG), fluorocarbon, and/or hydrocarbon.

27. The coating material of claim 26, wherein said coating material is (E)-PEG350-4-cyano-4-((E)-((R)-2-cyano-5-(6-mercaptohexylthio)-5-oxopenta-n-2-yl)diazenyl)pentanoic acid, (E)-PEG750-4-cyano-4-((E)-((R)-2-cyano-5-(6-mercaptohexylthio)-5-oxopenta-n-2-yl)diazenyl)pentanoic acid or (E)-PEG2000-4-cyano-4-((E)-((R)-2-cyano-5-(6-mercaptohexylthio)-5-oxopenta-n-2-yl)diazenyl)pentanoic acid, or a chemically similar coating material.

28. The coating material of claim 23, wherein said body has between 3 and 10,000 repeat units.

\* \* \* \* \*